(12) United States Patent
Bigham et al.

(10) Patent No.: US 6,187,789 B1
(45) Date of Patent: Feb. 13, 2001

(54) SUBSTITUTED ISOQUINOLINES AS ULTRA SHORT ACTING NEUROMUSCULAR BLOCKERS

(75) Inventors: Eric Cleveland Bigham, Chapel Hill; Grady Evan Boswell, Cary, both of NC (US); John Joseph Savarese, Southbury, CT (US); Roy Archibald Swaringen, Jr., Durham, NC (US); Sanjay Shashikant Patel, Cary, NC (US); Eric Eugene Boros, Chapel Hill, NC (US); Robert Anthony Mook, Jr., Chapel Hill, NC (US); Vincente Samano, Chapel Hill, NC (US)

(73) Assignees: Glaxo Wellcome Inc., Research Triangle Park, NC (US); Cornell Research Foundation Inc., Ithaca, NY (US)

( * ) Notice: Under 35 U.S.C. 154(b), the term of this patent shall be extended for 0 days.

(21) Appl. No.: 09/381,719

(22) PCT Filed: Mar. 23, 1998

(86) PCT No.: PCT/EP98/01651

§ 371 Date: Jan. 19, 2000

§ 102(e) Date: Jan. 19, 2000

(87) PCT Pub. No.: WO98/42674

PCT Pub. Date: Oct. 1, 1998

(30) Foreign Application Priority Data

Mar. 25, 1997 (GB) ................................. 9706117
Nov. 27, 1997 (GB) ................................. 9724987

(51) Int. Cl.[7] ........................ A61K 31/47; C07D 217/02; C07D 217/06; C07D 217/12

(52) U.S. Cl. ........................ 514/308; 514/307; 546/140; 546/144; 546/147

(58) Field of Search ................................. 514/307, 308; 546/140, 147, 144

(56) References Cited

U.S. PATENT DOCUMENTS 4,179,507  12/1979  Dewar et al. .
4,761,418  8/1988  Swaringen, Jr. et al. .

OTHER PUBLICATIONS

Nirmal C. Dhar, et al, "Approaches To Short–acting Neuromuscular Blocking Agents: Nonsymmetrical Bis–tetrahydroisoquinolinium Mono–0 and Diesters", Journal Of Medicinal Chemistry, vol. 39, No. 2, 1996, Washington, US, pp. 556–561.

*Primary Examiner*—D. Margaret Seaman
(74) *Attorney, Agent, or Firm*—Lorie Ann Morgan; Shah Makujina

(57) ABSTRACT

Ultrashort acting neuromuscular blocking agents of Formula (I) which are useful as skeletal muscle relaxants during emergency intubation procedures, routine surgery and post-operative settings are disclosed, wherein: X is a halogen; h is from 1 to 2; Y is hydrogen or methoxy; $Z^1$ and $Z^2$ are methyl; $W^1$ and $W^2$ are carbon; and A is a pharmaceutically acceptable anion.

7 Claims, No Drawings

SUBSTITUTED ISOQUINOLINES AS ULTRA SHORT ACTING NEUROMUSCULAR BLOCKERS

This application is filed pursuant to 35 U.S.C. § 371 as a United States National Phase Application of International Application No. PCT/EP98/01651 filed mar. 23, 1998, which claims priority from both GB 9706117.0 filed mar. 25, 1997 and GB 9724987.4 filed Nov. 27, 1997.

The present invention relates to novel compounds, methods for the preparation of such compounds, pharmaceutical compositions containing them and their use as neuromuscular blocking agents of ultra-short duration.

In anesthesia, neuromuscular blocking agents are used to provide skeletal muscle relaxation during surgery and during intubation of the trachea. Neuromuscular blockers are generally classified by both the mechanism of action (depolarizing or non-depolarizing) and the duration of action (ultrashort, short, intermediate, and long). See, Bedford, R., "From the FDA", *Anesthesiology,* 82(1), 33a. 1995. Non-depolarizing neuromuscular blocking agents include long-duration agents such as d-tubocurarine, pancuronium, gallamine, diallyltoxiferine and toxiferine, intermediate-duration agents such as atracurium and vecuronium, and short-duration agents such as mivacurium. See e.g., U.S. Pat. No. 4,179,507, U.S. Pat. No. 4,701,460, U.S. Pat. No. 4,761,418 and U.S. Pat. No. 5,945,510. Conventional non-depolarizing agents typically exhibit a 20 to 180 minute duration of action when used as skeletal muscle relaxants. Presently there are no ultrashort duration, non-depolarizing neuromuscular blocking agents in clinical use.

Depolarizing agents include succinylcholine and decamethonium. Due to their depolarizing mechanism of action, these agents can have severe side effects such as cardiac arrest and death, hyperkalemia, malignant hyperthermia, severe muscle pain, cardiac arrhythmias, increased intraocular pressure and increased intragastric tension. Conventional depolarizing agents exhibit shorter durations of action, e.g., 10 to 15 minutes in humans. Succinylcholine has a rapid onset and ultrashort duration of action and is the only ultra-short acting neuromuscular blocker in clinical use. Despite its undesirable side effect profile, no other ultrashort acting agent is available and thus it is currently the preferred agent for emergency use. The ultra-short duration of action is extremely important in emergency situations. Use of longer duration agents could lead to serious brain damage and death.

Non-depolarizing agents are generally believed to be safer and more clinically desirable than depolarizing agents, and clinicians have long recognized the need for a non-depolarizing neuromuscular blocker that has an ultra-short duration of action. See, Miller, R. D. *Anesthesia and Analgesia* 61(9), 721, 1982; and Belmont, M. R., *Current Opinion in Anaesthesiology,* 8, 362, 1995. However, non-depolarizing agents can exhibit side effects not specifically related to their mechanism or duration of action. For example, the long-duration agents pancuronium and gallamine have effects on the autonomic nervous system and may cause an increase in heart rate (tachycardia). Intermediate- and short-duration agents such as atracurium besylate and mivacurium chloride may also exhibit the side effect of histamine release. Histamine release has undesirable effects on blood pressure and heart rate, and some physicians believe that release of large amounts of histamine can cause life-threatening anaphylaxis in some patients.

It has now been discovered that compounds of Formula (I) include potent non-depolarizing neuromuscular blocking agents of ultra-short duration, e.g., about 5 to 15 minutes, that will provide both increased safety over known depolarizing ultrashort acting agents, e.g. succinylcholine, and a reduced capacity to release histamine over other non-depolarizing agents such as atracurium and mivacurium. In addition, they have a rapid onset of action and are reversed by treatment with known reversal agents such as neostigmine, both very important features in emergency situations and in other procedures. These agents maintain their ultrashort duration of action and rapid spontaneous recovery when administered by either bolus or continuous infusion and are without the cumulative effects observed with other neuromuscular blockers (pancuronium, vecuronium). Thus, compounds of the present invention should provide a significant advantage in the emergency, routine surgical, and post-operative settings.

Accordingly, the present invention provides compounds of Formula (I):

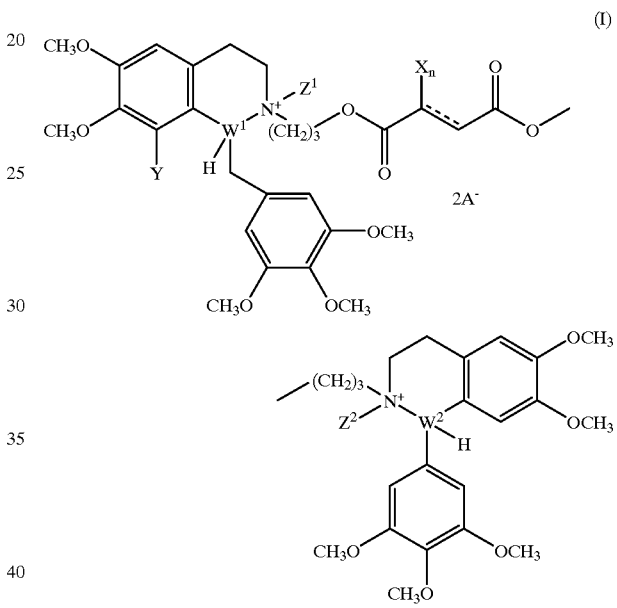

wherein X is halogen; h is from 1 to 2; Y is hydrogen or methoxy; $Z^1$ and $Z$ are methyl; $W^1$ and $W^2$ are carbon; and A is a pharmaceutically acceptable anion.

The compounds of Formula (I) contain two substituted isoquinolinium moieties connected by an aliphatic linker. The two substituted isoquinolinium moieties can be conveniently distinguished by referring to them as the "left head" and the "right head", where the left head contains $W^1$ and the right head contains $W^2$. The aliphatic linker is the portion of the compound of Formula (I) denoted by the following Formula (i).

The solid and dashed lines (------)indicates a double or single bond.

A suitable class of compounds of Formula (I) is that wherein X is chlorine or fluorine. Particularly preferred halogen substitutions are monochloro, monofluoro and difluoro.

The aliphatic linker portion of compounds of Formula (I), as described by Formula (i), comprises a butanedioate or butenedioate moiety. Suitably, compounds of Formula (I) wherein the aliphatic linker comprises a butenedioate moiety may exist in either the E or Z configuration or as mixtures of E and Z isomers. Preferably the to butenedioate moiety of compounds of Formula (I) is a fumarate.

The term fumarate as used herein refers to a butenedioate moiety wherein the two ester carbonyl groups are oriented trans to one another.

A preferred class of compounds of Formula (I) is that wherein the aliphatic linker is a butanedioate moiety and X represents chlorine or fluorine and h is 1 or 2. A particularly preferred class of compounds of Formula (I) is that wherein the aliphatic linker is a butanedioate moiety and X represents fluorine and h is 1 or 2. Compounds of Formula (I) wherein the aliphatic linker is a butanedioate moiety, X represents fluorine and h is 2 are most preferred.

Another preferred class of compounds of Formula (I) is that wherein the aliphatic linker is a butenedioate moiety and X represents chlorine or fluorine. A particularly preferred class of compounds of Formula (I) includes those wherein the aliphatic linker is a butenedioate moiety, X represents chlorine or fluorine, h is 1 and the butenedioate moiety is a fumarate. Compounds of Formula (I) wherein the aliphatic linker is a butenedioate moiety, X represents chlorine, h is 1 and the butenedioate moiety is a fumarate are most preferred.

The compounds of Formula (I) contain four chiral centres. The carbon atoms (denoted as $W^1$ and $W^2$) and each quaternary nitrogen atom in the isoquinolinium moieties are chiral. Each of the four chiral centres may independently exist in either the R or S configuration. Accordingly, it would be apparent to those skilled in the art that each compound within Formula (I) may exist in sixteen distinct optical isomeric forms. The scope of the present invention extends to cover each and every isomer of the compounds of Formula (I) either individually or in admixture with other isomers, and all mixtures of such isomers. Suitably $W^1$ is in the R configuration, the N attached to Z is in the S configuration, W is in either the R or S configuration, and the N attached to $Z^2$ is in either the R or S configuration. Preferably $W^1$ is in the R configuration, the N attached to $Z^1$ is in the S configuration, $W^2$ is in the S configuration, and the N attached to $Z^2$ is in either the R or S configuration. Compounds of Formula (I) wherein $W^1$ is in the R configuration, $W^2$ is in the S configuration, the N attached to $Z^1$ is in the S configuration and the N attached to $Z^2$ is in the R configuration are most preferred.

Particularly preferred compounds of Formula (I) include:
(Z)-2-Chloro-4-{3-[(1S,2R)-6,7-dimethoxy-2-methyl-1-(3, 4,5-trimethoxyphenyl)-1,2,3,4-tetrahydro-2-isoquinolinio]propyl}-1-{3{(1R,2S)-6,7-dimethoxy-2-methyl -1-[(3,4,5-trimethoxyphenyl)methyl]-1,2,3,4-tetrahydro-2-isoquinolinio}propyl}-2-butenedioate dichloride,
2,2-Difluoro-4-{3-[(1S,2R)-6,7-dimethoxy-2-methyl-1-(3, 4,5-trimethoxyphenyl)-1,2,3,4-tetrahydro-2-isoquinolinio]propyl}1-{3-{(1R,2S)-6,7-dimethoxy-2-methyl-1-[(3,4,5-trimethoxyphenyl)methyl]-1,2,3,4-tetrahydro-2-isoquinolinio} propyl}-butanedioate dichloride,
(Z)4-{3-[(1S,2R)-6,7-Dimethoxy-2-methyl-1-(3,4,5-trimethoxyphenyl)-1,2,3,4-tetrahydro-2-isoquinoliniolpropyl}-1-{3-{(1R,2S)-6,7-dimethoxy-2-methyl-1-[(3,4,5-trimethoxyphenyl)methyl]-1,2,3,4-tetrahydro-2-isoquinolinio} propyl}-2-fluoro-2-butenedioate dichloride and 2,2-Difluoro-4-{3-[(1S,2R)-6,7-dimethoxy-2-methyl-1-(3, 4,5-trimethoxyphenyl)-1,2,3,4-tetrahydro-2-isoquinolinio]propyl}-1-{3-{(1R,2S)-2-methyl-6,7,8-trimethoxy-1-[(3,4,5-trimethoxyphenyl)methyl]-1,2,3,4-tetrahydro-2-isoquinolinio}propyl}butanedioate dichloride.

Since the pharmacological activity of the compounds of the invention resides in the cation, the nature of the anion $A^-$ is relatively unimportant. However, for therapeutic purposes it is, preferably, pharmaceutically acceptable to the recipient of the compounds. Examples of pharmaceutically acceptable anions include iodide, mesylate, tosylate, bromide, chloride, hydrogen sulphate, sulphate/2, phosphate/3, hydrogen phosphates, acetate, besylate, succinate/2, maleate, naphthalenesulphonate and propionate. Both pharmaceutically acceptable salts and salts which are not thus acceptable may be useful for isolating and/or purifying the compounds of the invention. The unacceptable salts may also be useful in that they may be converted into acceptable salts by techniques well known in the art.

The compounds of Formula (I) are used as neuromuscular blocking agents during surgery, for intubation of the trachea or during electroshock therapy. They may be administered parenterally, e.g., by intramuscular or intravenous injection of a solution. Accordingly, the present invention also provides a method for producing muscle relaxation in a mammal, which comprises administering to the mammal an effective neuromuscular blocking amount of a compound of Formula (I). The dosage for each subject may vary, however, a suitable intravenous amount or dosage of the compounds of Formula (I) to obtain paralysis in mammals would be 0.01 to 5.0 mg/kg of body weight, and most preferably, 0.02 to 0.5 mg/kg of body weight, the above being based on the weight of the di-cation which is the active ingredient. The dosage for intramuscular administration is two to eight times the intravenous dose.

In a further aspect, the present invention provides compounds of Formula (I) for use in therapy, for example to induce neuromuscular blockade in surgery or for intubation of the trachea. The present invention also provides the use of a compound of Formula (I) in the manufacture of a medicament for inducing neuromuscular blockade in a mammal, including in a human.

While it is possible for the compounds of Formula (I) to be administered as the bulk active chemicals, it is preferred to present them in the form of a pharmaceutical formulation for parenteral administration. Accordingly, the present invention provides a pharmaceutical formulation which comprises a compound of Formula (I), as hereinbefore defined and a pharmaceutically acceptable carrier.

Where the pharmaceutical formulation is for parenteral administration, the formulation may be an aqueous or non-aqueous solution or mixture of liquids, which may contain bacteriostatic agents, antioxidants, buffers or other pharmaceutically acceptable additives. Alternatively the compounds may be presented as lyophilized solids for reconstitution with water (for injection) or dextrose or saline solutions. Such formulations are normally presented in unit dosage forms such as ampoules or disposable injection devices. They may also be presented in multi-dose forms such as a bottle from which the appropriate dose may be withdrawn. All such formulations should be sterile.

A suitable dose to obtain a neuromuscular block for adult humans (150 lbs. or 70 kg) is 0.5 to 150 mg and more preferably 3.5 to 50 mg. The compounds of this invention may optionally be administered before or after (but not simultaneously with) the depolarizing agents specified above. Thus a suitable pharmaceutical parenteral preparation for administration to humans will preferably contain 0.1 to 20 mg/ml of the compounds of Formula (I) in solution or multiples thereof for multi-dose vials.

A simple and preferred formulation is a solution of the compound of Formula (I) in water or dextrose solution. This may be prepared by dissolving the compound in pyrogen-free, sterile water or water containing dextrose, with or without a preservative and sterilizing the solution. Alternatively, it may be prepared by dissolving the sterile compound in pyrogen-free, sterile water or a sterile dextrose solution under aseptic conditions. Particularly preferred formulations have a pH of about 2.0 to 5.0.

The compounds of Formula (I) may also be administered as an infusion of a dextrose solution or saline solution, e.g., Ringer's solution in drip form.

The compounds may also be administered in other solvents (usually as a mixed solvent with water) such as alcohol, polyethylene glycol and dimethylsulphoxide. They may also be administered intramuscularly (as a drip if required) as a suspension a or solution.

General Description of Processes

Unless otherwise indicated, Y, $X_h$, and $A^-$ described in the formulae which follow are as defined in Formula (I) above. W corresponds to $W^1$ and $W^2$ of Formula (I), Z corresponds to $Z^1$ and $Z^2$ of Formula (I) and $X^1{}_h$ and $X^2{}_h$ correspond to $X_h$ of Formula (I). Unless otherwise specified T represents hydroxyl or halide.

Another aspect of the present invention is a process for the preparation of compounds of Formula (I). Compounds of Formula (I) may be prepared by reacting two equivalents of a compound of Formula (III):

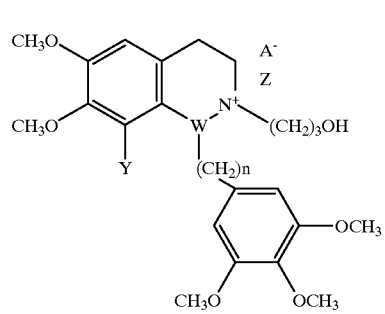

(III)

wherein Y is hydrogen or methoxy; Z is methyl; W is carbon; n is 0 or 1; and A is a pharmaceutically acceptable anion;
with one equivalent of a compound of Formula (VII):

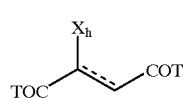

(VII)

in an aprotic solvent. The preferred method of coupling compounds of Formula (III) with compounds of Formula (VII) involves mixing the diacid or diacid chloride derivative of (VII) (wherein T is hydroxyl or halide, e.g. Cl) with two equivalents of a compound of Formula (III) in a chlorinated organic solvent at ambient or elevated temperatures.

A further aspect of the present invention provides another process for the preparation of compounds of Formula (I). Compounds of Formula (I) may be prepared by coupling two different compounds of Formula (III) with one equivalent of a compound of Formula (VII). Reactions of this type are preferably carried out by preparing an equimolar solution of two different compounds of Formula (III) in a chlorinated organic solvent followed by addition of one equivalent of a diacid chloride derivative of (VII) (e.g., T is Cl). This technique generates a statistical mixture of 3 different compounds of Formula (I) (ignoring stereochemical considerations and linker regiochemistry) and the major component of this mixture is always the compound of Formula (I) containing two different head groups; i.e., a mixed-head compound of Formula (I). One or more of these compounds may be separated from the mixture by chromatographic techniques. This may be followed by the introduction of pharmaceutically acceptable counterions ($A^-$) by conventional ion exchange techniques. Compounds of Formula (III) wherein n is 0 are novel intermediates for the preparation of compounds of Formula (I) and represent a further aspect of the invention.

Compounds of Formula (III) may be prepared by two general processes which form a further aspect of the invention. A first process involves quaternization of compounds of Formula (V) (defined herein):

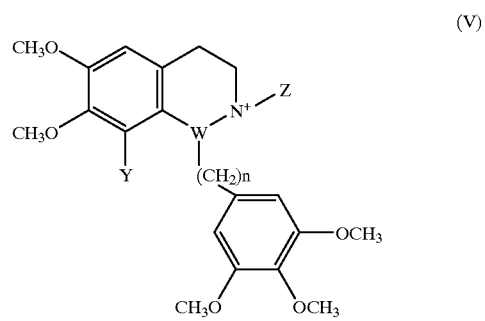

(V)

wherein Y is hydrogen or methoxy; Z is methyl; W is carbon, and n is 0 or 1 with compounds of Formula (VIII) (defined herein):

(VIII)

where the substituent A in (VIII) is a suitable leaving group (e.g., wherein A is I, Br, Cl, $OSO_2Me$, $OSO_2PhCh_3$) and corresponds to the anion, $A^-$; and optionally converting the anion ($A^-$) in the resulting compound of Formula (III) into another anion ($A^-$) by conventional ion exchange techniques. Reactions of compounds of Formula (V) with compounds of Formula (VIII) are preferably carried out in polar aprotic solvents at elevated temperatures in the presence of sodium carbonate. Compounds of Formula (III) prepared by this process are generated as mixtures of cis/trans stereoisomers and separation of cis/trans isomers of (III) typically requires chromatographic techniques, wherein the terms cis and trans refer to the spatial orientation of the aryl group attached to W relative to that of the alkanol group attached to N.

A second process for the preparation of compounds of Formula (III) involves alcoholysis or hydrolysis of zwitterionic compounds of Formula (IX) (defined herein):

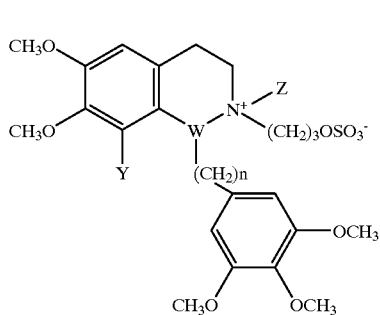

(IX)

wherein Y is hydrogen or methoxy; Z is methyl; W is carbon; and n is 0 or 1.

Alcoholysis of a compound of Formula (IX) may be performed in any suitable alcohol in the presence of a mineral acid and is preferably carried out in methanol solutions of hydrogen chloride at ambient temperature. Compounds of Formula (IX) are prepared by the quaternization of compounds of Formula (V) with cyclic sulfates of Formula (IV):

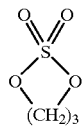

(IV)

Reactions of compounds of Formula (V) with compounds of Formula (IV) are preferably carried out in polar aprotic solvents at elevated temperatures. Compounds of Formula (IX) prepared by this process are generated as mixtures of cis/trans isomers; however, cis/trans mixtures of compounds of Formula (IX) may be separated by selective crystallization of the trans isomer of compounds of Formula (IX) from the mixture. Selective crystallization of trans isomers of compounds of Formula (IX) are preferably accomplished with polar aprotic solvents such as acetonitirile or acetone. This process is the preferred method of preparation of compounds of Formula (III), especially trans isomers of compounds of Formula (III) where the alkanol side chain (($CH_2)_3OH$) and the phenyl (n=0) or benzyl (n=1) substituent are oriented trans to one another in space, and represents a further aspect of the present invention. Compounds of Formula (IX) are novel intermediates and represent another aspect of the invention.

Another aspect of the invention comprises a novel process for the preparation of compounds of Formulae (I) and (II). The preparation of compounds of Formula (I) involves coupling a compound of Formula (II):

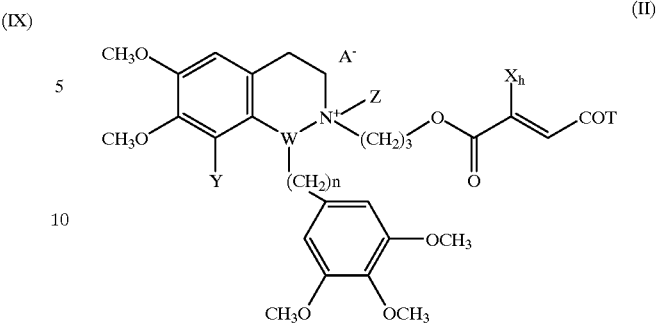

(II)

wherein T is hydroxyl or halide; Y is hydrogen or methoxy; Z is methyl; W is carbon; n is 0 or 1; h is 1 or 2; and A is a pharmaceutically acceptable anion to a compound of Formula (III).

These reactions are preferably carried out by addition of a compound of Formula (III) to the acid or acid chloride derivative of (II) (wherein T is hydroxyl or halide, e.g. Cl) in a chlorinated organic solvent at ambient or elevated temperatures. The acid chloride derivatives of compounds of Formula (II) (e.g., wherein T is Cl) may be prepared from the corresponding carboxylic acids of compounds of Formula (II) (e.g., wherein T is OH) by methods well known to those skilled in the art.

Compounds of Formula (II) (e.g., wherein T is OH) are obtained by ring opening of compounds of Formula (VI) (defined herein):

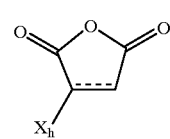

(VI)

with compounds of Formula (III). These reactions are preferably carried out by mixing compounds of Formulae (III) and (VI) in chlorinated organic solvents at ambient or elevated temperatures. If necessary, these reactions may be facilitated by the addition of a catalyst such as imidazole. These methods may be followed by the introduction of pharmaceutically acceptable counterions (A⁻) by conventional ion exchange techniques. Ring opening of halogenated cyclic anhydrides of compounds of Formula (VI) (e.g., X is Cl or F) with compounds of Formula (III) can occur selectively to give compounds of Formula (II) (e.g., X is Cl or F; T is OH). In these reactions, the hydroxyl group of (III) reacts preferentially at the carbonyl group of compounds of Formula (VI) adjacent to the halogen atom. This process is the preferred method for the preparation of mixed-head compounds of Formula (I). Compounds of Formula (II) are novel intermediates in the preparation of compounds of Formula (I) and represent another aspect of the invention.

A further aspect of the present invention provides a process for the conversion of one compound of Formula (II) into another compound of Formula (II). Monohalogenated alkenedioates of Formula (IIb) (e.g., X is Cl or F; h is 1):

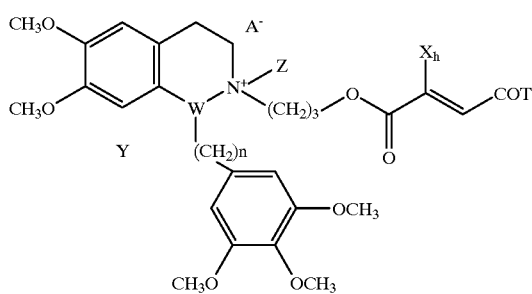

(IIb)

may be prepared by a process which involves elimination of hydrogen halide (HX$^2$) from vicinal dihalo alkanedioates of Formula (IIa) (e.g., X$^1$ and X$^2$ are independently Cl or F; T is hydroxyl or halide; h is 1):

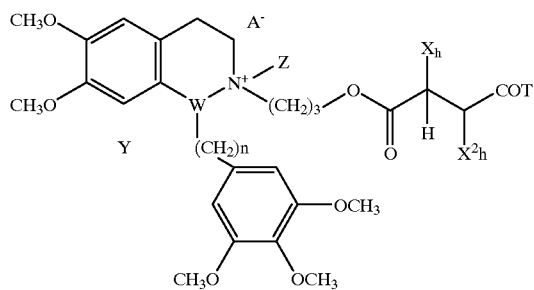

(IIa)

Compounds of Formula (IIa) are prepared by the reaction of compounds of Formula (III) with compounds of Formula (VIa) (X=Br, Cl, F and h is 1):

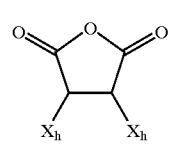

(VIa)

These reactions are preferably carried out by mixing compounds of Formulae (III) and (VIa) in chlorinated organic solvents at ambient or elevated temperatures. If necessary, these reactions may be facilitated by the addition of a catalyst such as imidazole. These methods may be followed by the introduction of pharmaceutically acceptable counterions (A$^-$) by conventional ion exchange techniques.

The transformation of compounds of Formula (IIa) into compounds of Formula (IIb) is typically performed by treatment of (IIa) with an excess of a tertiary amine, such as triethyl amine, in polar aprotic or chlorinated organic solvents at 0° C. In this elimination process, the hydrogen atom (H) vicinal to the ester carbonyl oxygen in (IIa) (α to the ester carbonyl) is abstracted selectively. The resulting compounds of Formula (IIb) may be converted to monohalogenated alkenedioates of Formula (I) by methods described herein.

Another aspect the present invention provides a process for the conversion of one compound of Formula (I) into another compound of Formula (I). Monohalogenated alkenedioates of Formula (Ib):

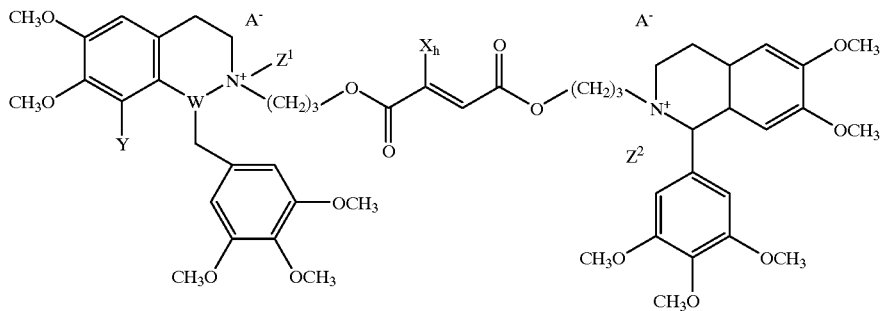

(Ib)

may be prepared by elimination of hydrogen halide (HX) from geminal dihalo alkanedioates of Formula (Ia) (e.g., X is Cl or F; h is 2).

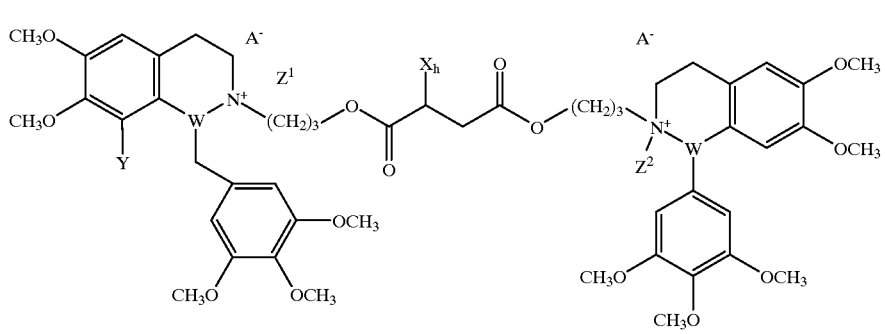

(Ia)

Elimination of HX from compounds of Formula (Ia) are preferably carried out with potassium carbonate in polar aprotic solvents, such as dimethylformamide, at ambient temperature.

Mixed head monohalobutenedioates of Formula (I) (e.g., X is Cl or F; h is 1) exist as 1:1 mixtures of regioisomers when synthesized by said process which comprises reacting two equivalents of a compound of Formula (III) with one equivalent of a compound of Formula (VII). However, mixed head monohalobutenedioates of Formula (I) (e.g., X is Br, Cl, F; h is 1) exist as pure regioisomers when synthesized by said processes comprising conversion of compounds of Formulae (Ia) to (Ib) or conversion of compounds of Formulae (IIa) to (IIb). Thus, the latter two processes are preferred methods for the preparation of mixed head monohalobutenedioates of Formula (I).

Alkenedioate derivatives of Formulae (I) and (II) may exist as E and Z geometric isomers; however, monohalogenated butenedioate analogs of Formula (I) preferentially exist as halofumarates such that the two ester carbonyl groups are oriented trans to one another. Compounds of Formula (I) may also exist as mixtures of diastereomers and one or more diastereomers may be separated from the mixture by conventional techniques; for example, chromatographic techniques.

Compounds of Formulae (IV), (V) and (VI), diacid chloride derivatives of (VII) and compounds of Formula (VIII) are commercially available or may be prepared by published processes for the preparation of the same or structurally analogous compounds. Pure enantiomers of (V) are obtained by published asymmetric synthetic methods, known classical resolution techniques, or chiral preparative HPLC.

Experimental

Melting points are uncorrected. All reagent chemicals were used without purification. Analytical high performance liquid chromatography (HPLC) analyses were performed on a 4×250 mm 5µ Si60 LiChrosorb column (E. Merck, Darmstadt, Germany) at a flow rate of 1.6 mL/min. The mobile phase consisted of 0–25% methanol (MeOH)/ dichloromethane ($CH_2Cl_2$) mixtures containing 0.25 mL of methanesulfonic acid/L. Medium pressure liquid chromatography (MPLC) separations were performed on twin Porasil 15–20µ cartridges (Waters/Millipore, Milford. Mass., USA) eluting with 0–20% MeOH/$CH_2Cl_2$ mixtures containing 0.25 mL of methanesulfonic acid/L. Proton nuclear magnetic resonance ($^1$NMR) spectra of all products were consistent with the proposed structures. Positive ion flow injection electrospray mass spectra (MS) are reported in the form m/z (doubly charged positive ion, relative intensity). Elemental analyses were performed by Atlantic Microlab, Norcross, Ga.

Chlorofumaryl chloride was prepared by a reported procedure (Akhtar, M.; Botting, P. N.; Cohen, M. A. *Tetrahedron* 1987, 43, 5899–5908).

3,4-Dihydroisoquinoline derivatives were prepared by Bishler-Napieralski cyclization of the corresponding amides with phosphorous oxychloride (Whaley, K. W.; Govindachari *Org. Reactions* 1951, 6, 74–150). Racemic 1,2,3,4-tetrahydroisoquinoline derivatives were prepared by reduction of their 3,4-dihydroisoquinoline precursors with sodium borohydride/methanol. N-Methylations of 1,2,3,4-tetrahydroisoquinoline derivatives were carried out with formaline/formic acid (Kaluszyner, A.; Galun A. B. *J. Org. Chem.* 1961, 26, 3536–3537).

The following starting materials were prepared by chiral catalytic hydrogenation of their corresponding 3,4-dihydroisoquinolines by a procedure similar to that described by Noyori et al. (Uematsu, N.; Fujii, A.; Hashiguchi. S.; Ikariya, T.; Noyori, R. *J. Am. Chem. Soc.* 1996, 118,4916–4917) followed by N-methylation:
(1R)-6,7-Dimethoxy-2-methyl-1-(3,4,5-trimethoxyphenyl)-1,2,3,4-tetrahydroisoquinoline;
(1S)-6,7-Dimethoxy-2-methyl-1-(3,4,5-trimethoxyphenyl)-1,2,3,4-tetrahydroisoquinoline.

The following starting material was obtained by classical resolution of its corresponding 3,4-dihydroisoquinoline derivative by a procedure similar to that described by Brossi et al. (Brossi, A.; Teitel, S. *Helv. Chim. Acta* 1973, 54, 1564–1571) followed by N-methylation:
(1R)-6,7-Dimethoxy-2-methyl-1-(3,4,5-trimethoxyphenyl)-1,2,3,4-tetrahydroisoquinoline; and
(1S)-6,7-Dimethoxy-2-methyl-1-(3,4,5-trimethoxyphenyl)-1,2,3,4 -tetrahydroisoquinoline;.

The following starting materials were obtained by classical resolution of their corresponding racemic mixtures by a procedure similar to that described by Swaringen et al. (U.S. Pat. No. 4,761,418 Aug. 2, 1988):
(R)-(−)-5'-Methoxylaudanosine;
(S)-(+)-5'-Methoxylaudanosine; and
(1R)-2-Methyl-6,7,8-trimethoxy-1-[(3,4,5-trimethoxyphenyl)methyl]-1,2,3,4-tetrahydroisoquinoline.

SYNTHETIC EXAMPLE 1

(a) (1S,2R)- and (1S,2S)-6,7-Dimethoxy-2-(3-hydroxypropyl)-2-methyl-1-(3,4,5-trimethoxyphenyl)-1,2,3,4-tetrahydroisoquinolinium chloride To a mixture of (1s)-6,7-Dimethoxy-2-methyl-1-(3,4,5-trimethoxyphenyl)-1,2,3,4-tetrahydroisoquinoline (56.0 g, 0.15 mol), sodium iodide (45.0 g, 0.30 mol), sodium carbonate (4.0 g, 0.038 mol), and 2-butanone (600 mL) was added 3-chloropropanol (25.0 mL, 28.3 g, 0.30 mol) and the suspension was heated to reflux for 18hours (h) under nitrogen atmosphere. Solvent was evaporated and the residue was dissolved in $H_2O$ and washed with ethyl acetate (EtOAc). The aqueous phase was stirred with Dowex 1×8–50 (1.0 L), filtered, and saturated with sodium chloride. The aqueous mixture was extracted with chloroform ($CHCl_3$) and the combined organic layers were dried and concentrated to provide a 3:1 mixture of the (1S,2R)- and (1S,2S)-title products, respectively as a white solid (69.5 g, 99% yield): MS m/z 432 ($M^+$, 9).

(b) (1R,2S)- and (1R,2R)-6,7-Dimethoxy-2-(3-hydroxypropyl)-2-methyl-1-[(3,4,5-trimethoxyphenyl)methyl]-1,2,3,4-tetrahydroisoquinolinium chloride (R)-(−)-5'-Methoxylaudanosine (23.5 g, 61.0 mmol) was subjected to a procedure to give a 2.3:1 mixture of the (1R,2S)- and (1R,2R)-title products, respectively as a yellow, hygroscopic solid (31.5 g, 100% yield). The isomers were separated by MPLC (12% $MeOH/CH_2Cl_2$, 0.25 ml methanesulfonic acid/L). The minor (1R,2R) isomer eluted first. The appropriate fractions were combined and most of the MeOH was removed by coevaporation with $CHCl_3$. The remaining $CHCl_3$ solution was washed with 1:1 brine/$H_2O$, dried and concentrated to provide the (1R,2S)-title product (10.4 g, 35% yield) and the (1R,2R)-title product (3.7 g, 13% yield) as yellow hygroscopic solids: MS (each isomer) m/z 446 ($M^+$, 100).

Example 1.01

(c) (Z)-2-Chloro-1-{3-[(1S,2R)-6,7-dimethoxy-2-methyl-1-(3,4,5-trimethoxyphenyl)-1,2,3,4-tetrahydro-2-isoquinolinio]propyl}-4-{3-{(1R,2S)-6,7-dimethoxy-2-methyl-1-[(3,4,5-trimethoxyphenyl)methyl]-1,2,3,4-tetrahydro-2-isoquinolinio}propyl}-2-butenedioate dichloride and (Z)-2-Chloro-4-{3-[(1S,2R)-6,7-dimethoxy-2-methyl-1-(3,4,5-trimethoxyphenyl)-1,2,3,4-tetrahydro-2-isoquinolinio]propyl}-1-{3-{(1R,2S)-6,7-dimethoxy-2-methyl-1-1[(3,4,5-trimethoxyphenyl)methyl]-1,2,3,4-tetrahydro-2-isoquinolinio}propyl}-2-butenedioate dichloride (1:1)

To a solution of the product mixture from step a (2.4 g, 5.1 mmol) and the (1R,2S)-isomer from step b (2.34 g, 4.9 mmol) in 1,2-dichloroethane (DCE) (30 mL) was added chlorofumaryl chloride (0.83 g, 4.4 mmol) and the solution was stirred at room temperature (rt) for 18 h. The solvent was evaporated and the remaining residue was purified by MPLC (5–20% $MeOH/CH_2Cl_2$, 0.25 mL methanesulfonic acid/L). The appropriate fractions were combined and most of the MeOH was removed by coevaporation with $CHCl_3$. The remaining $CHCl_3$ solution was washed with 1:1 brine/$H_2O$, dried and concentrated. Lyophilization provided a 1:1 mixture of the title products as a white solid (0.70 g, 15% yield): MS m/z 496 ($M^{2+}$, 100).

The following compounds were prepared by a procedure similar to Synthetic Example 1:

Example 1.02

(Z)-2-Chloro-1-{3-[(1R,2S)-6,7-dimethoxy-2-methyl-1-(3,4,5-trimethoxyphenyl)-1,2,3,4-tetrahydro-2-isoquinolinio]propyl}-4-{3-{(1R,2S)6,7-dimethoxy-2-methyl-1-[(3,4,5-trimethoxyphenyl)methyl]-1,2,3,4-tetrahydro-2-isoquinolinio}propyl}-2-butenedioate dichloride and (Z)-2-Chloro-4-{3-[(1R,2S)-6,7-dimethoxy-2-methyl-1-(3,4,5-trimethoxyphenyl)-1,2,3,4-tetrahydro-2-isoquinolinio]propyl}-1-{3-{(1R,2S)-6,7-dimethoxy-2-methyl-1-[(3,4,5-trimethoxyphenyl)methyl]1,2,3,4-tetrahydro-2-isoquinolinio]propyl}-2-butenedioate dichloride (1:1)

MS m/z 496 ($M^{2+}$, 100).

Example 1.03

(Z)-2-Chloro-1-{3-[(1S,2R)-6,7-dimethoxy-2-methyl-1-(3,4,5-trimethoxyphenyl)-1,2,3,4-tetrahydro-2-isoquinolinio]propyl}-4-{3-{(1R,2S)-2-methyl-6,7,8-trimethoxy-1-[(3,4,5-trimethoxyphenyl)methyl]-1,2,3,4-tetrahydro-2-isoquinolinio}propyl}-2-butenedioate dichloride and (Z)-2-Chloro-4-{3-[(1S,2R)-6,7-dimethoxy-2-methyl-1-(3,4,5-trimethoxyphenyl)-1,2,3,4-tetrahydro-2-isoquinolinio]propyl}-1-{3-{(1R,2S)-2-methyl-6,7,8-trimethoxy-1-[(3,4,5-trimethoxyphenyl)methyl]-1,2,3,4-tetrahydro-2-isoquinolinio}propyl)-2-butenedioate dichloride (1:1)

MS m/z 511 ($M^{2+}$, 100).

Example 1.04

(Z)-2-Chloro-1-{3-[(1R,2S)-6,7-dimethoxy-2-methyl-1-(3,4,5-trimethoxyphenyl)-1,2,3,4-tetrahydro-2-isoquinolinio]propyl}-4-{3-{(1R,2S)-2-methyl-6,7,8-trimethoxy-1-[(3,4,5-trimethoxyphenyl)methyl]-1,2,3,4-tetrahydro-2-isoquinolinio}propyl}-2-butenedioate dichloride and (Z)-2-Chloro-4-{3-[(1R,2S)-6,7-dimethoxy-2-methyl-1-(3,4,5-trimethoxyphenyl)-1,2,3,4-tetrahydro-2-isoquinolinio]propyl}-1-{3-[(R,2S)-2-methyl-6,7,8-trimethoxy-1-(3,4,5-trimethoxyphenyl)methyl]-1,2,3,4-tetrahydro-2-isoquinolinio}propyl}-2-butenedioate dichloride (1:1)

MS m/z 511 ($M^{2+}$, 22).

SYNTHETIC EXAMPLE 2

(Method A)

(a) (2R*,3R*)-2,3-Dichlorosuccinic anhydride

A solution of maleic anhydride (10.6 g, 108 mmol) and benzoyl peroxide (5 mg, 0.02 mmol) in $CHCl_3$ (250 mL) was saturated with chlorine gas and the resulting bright yellow solution was stirred for 5 h at rt. Residual chlorine was removed with a stream of nitrogen and the reaction mixture was partially concentrated. Four crops of the white, solid title product were obtained by filtration (11.9 g, 65% yield): mp 90–92° C.

(b) (Z)-2-Chloro-1-{3-[(1R,2S)-6,7-dimethoxy-2-methyl-1-[(3,4,5 -trimethoxyphenyl)methyl]-1,2,3,4-tetrahydro-2-isoquinolinio}propyl}hydrogen 2-butenedioate monochloride A solution of the (1R, 2S)-title product from Synthetic Example 1, step b (3.5 g, 6.10 mmol) and the product from step a (1.7 g, 10.1 mmol) in DCE (38 mL) and acetonitrile (MeCN) (2 mL) was stirred at rt overnight. The mixture was concentrated and the remaining solid was triturated with EtOAc and dissolved in MeCN (25 mL). A solution of 1,8-diazabicyclo[5.4.0]undec-7-ene (DBU) (1.68 g, 11.0 mmol) in MeCN (6 mL) was added dropwise at 0° C. and the reaction mixture was stirred at ice bath temperature for 1 h. The solvent was evaporated and the remaining solid was dissolved in $CHCl_3$ (150 mL). This solution was washed with 2:1 brine/water containing methanesulfonic acid (4 mg/mL) and with brine. The organic layer was dried and concentrated to provide the title product as a foam (2.6 g, 69% yield): MS m/z 578 ($M^+$, 100).

Example 2.01

(c) (Z)-2-Chloro-4-{3-[(1S,2R)-6,7-dimethoxy-2-methyl-1-(3,4,5-trimethoxyphenyl)-1,2,3,4-tetrahydro-2-isoquinolinio]propyl}-1-{3-{(1R,2S)-6,7-dimethoxy-2- methyl-1-(3,4,5-trimethoxyphenyl)methyl]-1,2,3,4-tetrahydro-2-isoquinolinio}propyl}-2-butenedioate dichloride A solution of oxalyl chloride (36 mmol) in $CH_2Cl_2$ (18 mL) was added dropwise to a stirring solution of the product from step b (2.22 g, 3.61 mmol) in DCE (25 mL). The reaction mixture was stirred 1 h at rt and then heated at reflux for 5 min. Excess oxalyl chloride was removed in vacuo and the resulting foam was dissolved in DCE (15 mL). A solution of the product mixture from Synthetic Example 1, step a (2.00 g, 3.58 mmol) in DCE (5 mL) was added and the solution was stirred overnight at rt. The solvent was evaporated and the mixture was purifed by MPLC as described in Synthetic Example 1, step c. Lyophilization provided the title product as a white solid (731 mg, 19% yield): MS m/z 496 ($M^{2+}$, 100).

The following compounds were prepared by a procedure similar to Synthetic Example 2:

Example 2.02

(Z)-2-Chloro-4-{3-[(1S,2S)-6,7-dimethoxy-2-methyl-1-(3,4,5-trimethoxyphenyl)-1,2,3,4-tetrahydro-2-isoquinolinio]propyl}-1-{3-{(1R,2S)-6,7-dimethoxy-2-methyl-1-[(3,4,5-trimethoxyphenyl)methyl]-1,2,3,4-tetrahydro-2-isoquinolinio}propyl}-2-butenedioate dichloride
MS m/z 496 ($M^{2+}$, 100).

Example 2.03

(Z)-2-Chloro-4-{3-[(1S,2R)-6,7-dimethoxy-2-methyl-1-(3,4,5-trimethoxyphenyl)-1,2,3,4-tetrahydro-2-isoquinolinio]propyl}-1-{3-{(1R,2S)-2-methyl-6,7,8-trimethoxy-1-[(3,4,5-trimethoxyphenyl)methyl]-1,2,3,4-tetrahydro-2-isoquinolinio}propyl}-2-butenedioate dichloride
MS m/z 511 ($M^{2+}$, 100).

Example 2.04

(Z)-2-Chloro-4-{3-[(1R,2S)-6,7-dimethoxy-2-methyl-1-(3,4,5-trimethoxyphenyl)-1,2,3,4-tetrahydro-2-isoquinolinio]propyl}-1-{3-{(1R,2S)-2-methyl-6,7,8-trimethoxy-1-[(3,4,5-trimethoxyphenyl)methyl]-1,2,3,4-tetrahydro-2-isoquinolinio}propyl}-2-butenedioate dichloride
MS m/z 511 ($M^{2+}$, 100).

SYNTHETIC EXAMPLE 3

(Method B): Alternative method for the preparation of the compound of Example 2.01

(a) 1,3-Dioxa-2-thiane 2,2-dioxide
To a solution of 1,3-propanediol (50.0 g, 0.65 mol) in carbon tetrachloride ($CCl_4$) (650 mL) was added thionyl chloride (57.5 mL, 93.7 g, 0.79 mol) and the mixture was heated to reflux for 1.5 h. The solution was cooled to 0° C. and diluted with MeCN (650 mL) followed by sequential addition of ruthenium (III) chloride hydrate (81 mg, 0.39 mmol), sodium periodate (210.0 g, 0.98 mol), and $H_2O$ (980 mL). The resulting orange mixture was stirred at rt for 1.5 h and then diluted with diethyl ether ($Et_2O$) (6 L). The separated organic phase was washed with water, saturated $NaHCO_3$ and brine. The $Et_2O$ layer was dried and filtered through a bed of silica gel. The filtrate was concentrated and the resulting oil was treated with $Et_2O$ (50 mL) and hexanes (100 mL) and stored at 5° C. for 18 h. Filtration of the resulting precipitate afforded the title compound as an off-white solid (79.0 g, 87% yield): mp 54–56° C.

(b) 3-[(1S,2R)-6,7-Dimethoxy-2-methyl-1-(3,4,5-trimethoxyphenyl)-1,2,3,4-tetrahydro-2-isoquinoliinio]propyl-1-sulfate
A mixture of (1S)-6,7-dimethoxy-2-methyl-1-(3,4,5-trimethoxyphenyl)-1,2,3,4-tetrahydroisoquinoline (36.8 g, 98.6 mmol) and the product from step a (23.7 g, 171.7 mmol) in MeCN (350 mL) was heated at 65° C. for 5 h. The mixture was cooled to rt and the resulting precipitate was collected by filtration and triturated with MeCN to afford the title compound as an off-white powder (30.0 g, 60% yield): mp 207–209° C.; MS m/z 534 (M+23, 60), 512 (M+1, 30), 432 ($M-SO_3$, 100).

(c) (1S,2R)-6,7-Dimethoxy-2-(3-hydroxypropyl)-2-methyl-1-(3,4,5-trimethoxyphenyl)-1,2,3,4-tetrahydroisoquinolinium chloride
Acetyl chloride (35.0 mL, 38.8 g, 0.49 mol) was added dropwise to ice-cold MeOH (350 mL) and the resulting solution was stirred for 10 minutes (min). The product from step b (28.1 g, 0.05 mol) was added and the reaction mixture was stirred at rt for 6 h. The solution was neutralized by careful addition of excess $NaHCO_3$ and the solid was filtered through a pad of celite. The filtrate was evaporated and the residue was dissolved in $CHCl_3$. The resulting solid was filtered through a pad of celite and washed with $CHCl_3$. The filtrate was evaporated, the remaining residue was dissolved in $H_2O$, and the aqueous solution was saturated with sodium chloride. The aqueous phase was extracted with $CHCl_3$ and the organic layers were dried and concentrated to give the title compound as a hygroscopic white solid (25.0 g, 98% yield): MS m/z 432 ($M^+$, 100).

(d) 3-{(1R,2S)-6,7-Dimethoxy-2-methyl-1-[(3,4,5-trimethoxyphenyl)-methyl]-1,2,3,4-tetrahydro-2-isoquinolinio}propyl-1-sulfate
(1R)-(−)-5'-Methoxylaudanosine (52.6 g, 0.13 mmol) was subjected to procedure b. The resulting material was triturated with acetone to yield the title product as an off-white powder (49.3 g, 69% yield): mp 191–193° C.; MS m/z 526 (M+1, 100).

(e) (1R,2S)-6,7-Dimethoxy-2-(3-hydroxypropyl)-2-methyl-1-[(3,4,5 trimethoxyphenyl)methyl]-1,2,3,4-tetrahydroisoquinolinium chloride
The product from step d (54.5 g, 0.10 mmol) was subjected to procedure c to afford the title compound as a hygroscopic white foam (50.7 g, 100% yield): MS m/z 446 ($M^+$, 100).

(f) (Z)-2-Chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}hydrogen 2-butenedioate monochloride
A solution of the product from step e (15 g, 31.1 mmol) and the product from Synthetic Example 2, step a (6.4 g, 37 mmol) in $CH_2Cl_2$ (50 mL) was stirred overnight at rt. The reaction mixture was diluted with $CH_2Cl_2$ (150 mL), cooled to −20° C. and triethylamine (18.2 mL, 130.4 mmol) was added dropwise. The reaction was warmed to 0C, $CHCl_3$ (200 mL) was added and the mixture was washed with 2:1 brine/water containing methanesulfonic acid (4 mg/mL). The $CHCl_3$ layer was separated and the combined aqueous layers were saturated with sodium chloride, acidified with concentrated hydrochloric acid (HCl) (9 mL) and back-extracted with $CHCl_3$. The combined $CHCl_3$ layers were dried and concentrated and the resulting foam was triturated with $Et_2O$. The title product was collected by filtration as a tan solid (16.3 g, 86% yield): spectral data identical to that of the title product from Synthetic Example 2, step b.

Example 3.01

(g) (Z)-2-Chloro-4-{3-[(1S,2R)-6,7-dimethoxy-2-methyl-1-(3,4,5-trimethoxyphenyl)-1,2,3,4-tetrahydro-2-isoquinolinio]propyl}-1-{3-{(1R,2S)6,7-dimethoxy-2-methyl-1-[(3,4,5-trimethoxyphenyl)methyl]-1,2,3,4-tetrahydro-2-isoquinolinio}propyl}-2-butenedioate dichloride The product from step f (7.0 g, 11.4 mmol) was treated with oxalyl chloride and then reacted with the product from step c (6.62 g, 11.9 mmol) as described in Synthetic Example 2, step c. The reaction mixture was concentrated and the resulting material was purified by MPLC as described in Synthetic Example 1, step c. Lyophilization provided the title product as a white solid (8.7 g, 72% yield): spectral data identical to that of the title product from Synthetic Example 2, step c.

SYNTHETIC EXAMPLE 4

(Method C) Alternative method for the preparation of the compounds of Examples 2.01 or 3.01

(a) (E)-2-Chloro-1-{3-{(1R,2S)-6,7-dimethoxy-2-methyl-1-[(3,4,5-trimethoxyphenyl)methyl]-1,2,3,4-tetrahydro-2-isoquinolinio}propyl}hydrogen 2-butenedioate monochloride To a solution of the product from Synthetic Example 3, step e (2.5 g, 5.2 mmol) and imidazole (0.35 g, 5.2 mmol) in $CH_2Cl_2$ (35 mL) at −15° C. was added a solution of chloromaleic anhydride (0.69 g, 5.2 mmol) in $CH_2Cl_2$ (10 mL). After 10 min, the mixture was diluted with $CHCl_3$ and washed with 2:1 brine/$H_2O$ containing methanesulfonic acid (4 mg/mL). The organic layers were washed with brine, dried and evaporated to give the title compound as a yellow hygroscopic solid: MS m/z 578 ($M^+$, 100).

Example 4.01

(b) (Z)-2-Chloro-4-{3-[(1S,2R)-6,7-dimethoxy-2-methyl-1-(3,4,5trimethoxyphenyl)-1,2,3,4-tetrahydro-2-isoquinolinio]propyl}-1-{3-{(1R,2S)-6,7-dimethoxy-2-methyl-1-[(3,4,5-trimethoxyphenyl)methyl]-1,2,3,4-tetrahydro-2-isoquinolinio}propyl}-2-butenedioate dichloride A solution of the product from step a (198 mg, 0.32 mmol), oxalyl chloride (281 μL, 3.2 mmol), and dimethyl formamide (DMF) (1 drop) in $CH_2Cl_2$ (4 mL) was heated at reflux for 2 h. The mixture was coevaporated with $CH_2Cl_2$ and dried in vacuo. The residue was dissolved in DCE (5 mL), the product mixture from Synthetic Example 1, step a (300 mg, 0.64 mmol) was added and the mixture was stirred at rt for 18 h. The solvent was evaporated and the crude material was purified as described in Synthetic Example 1, step c. Lyophilization provided the title product as a white solid (80 mg, 23% yield): spectral data identical to that of the title product from Synthetic Example 2, step c.

The following compound was prepared by a procedure similar to Synthetic Example 4:

Example 4.02

(Z)-2-Bromo-4-{3-[(1S,2R)6,7-dimethoxy-2-methyl-1-(3,4,5-trimethoxyphenyl)-1,2,3,4-tetrahydro-2-isoquinolinio]propyl}-1-{3-{(1R,2S)-6,7-dimethoxy-2-methyl-1-[(3,4,5-trimethoxyphenyl)methyl]-1,2,3,4-tetrahydro-2 isoquinolinio}propyl}-2-butenedioate dibromide MS m/z 518 ($M^{2+}$, 100).

SYNTHETIC EXAMPLE 5

(Method A)

(a) 2,2-Difluorosuccinic anhydride

A mixture of 2,2-difluorosuccinic acid (1.15 g, 7.46 mmol), thionyl chloride (4 mL, 20.6 mmol) and benzene (4 mL) was heated at reflux for 2.5 h. The mixture was filtered and the filtrate was concentrated to afford the title product as an oil that crystallized on standing (838 mg, 6.16 mmol, 83% yield).

(b) 2,2-Difluoro-1-{3-{(1R,2SR)-6,7-dimethoxy-2-methyl-1-[(3,4,5 trimethoxyphenyl)methyl]-1,2,3,4-tetrahydro-2-isoquinolinio}propyl}hydrogen butanedioate monochloride A solution of the 2.3:1 product mixture from Synthetic Example 1, step b (2.7 g, 5.60 mmol) and the product from step a (838 mg, 6.16 mmol) in DCE (80 mL) was stirred overnight at rt. The solvent was evaporated to yield a 2.3:1 mixture of the (1R, 2S)- and (1R, 2R)-title products, respectively as a yellow hygroscopic solid (3.5 g, 5.60 mmol, 100% yield): MS m/z 582 ($M^+$, 70).

Example 5.01

(c) 2,2-Difluoro-4-{3-[(1S,2R)-6,7-dimethoxy-2-methyl-1-(3,4,5-trimethoxyphenyl)-1,2,3,4-tetrahydro-2-isoquinolinio]propyl}1-{3-{(1R,2S)-6,7-dimethoxy-2-methyl-1-[(3,4,5-trimethoxyphenyl)methyl]-1,2,3,4-tetrahydro-2-isoquinolinio}propyl}-butanedioate dichloride The product mixture from step b (2.0 g. 3.24 mmol) was treated with oxalyl chloride and then reacted with the product mixture from Synthetic Example 1, step a (1.73 g, 3.10 mmol) as described in Synthetic Example 2. step c. The reaction mixture was concentrated and the resulting material was purified by MPLC as described in Synthetic Example 1. step c. Lyophilization provided the title product as a white solid (466 mg, 27% yield): MS m/z 498 ($M^{2+}$, 100).

SYNTHETIC EXAMPLE 6

(Method B): Alternative method for the preparation of the compound of Example 5.01

(a) 2,2-Difluoro-1-{3-{(1R,2S)-6,7-dimethoxy-2-methyl-1-[(3,4,5-trimethoxyphenyl)methyl]-1,2,3,4-tetrahydro-2-isoquinolinio}propyl}hydrogen butanedioate monochloride The product from Synthetic Example 3, step e (3.0 g, 6.22 mmol) was treated in a fashion similar to that described in Synthetic Example 5, step b. The title product was obtained as a yellow hygroscopic solid (3.21 g, 83% yield): spectral data were consistent with the proposed structure.

Example 6.01

(b) 2,2-Difluoro-4-{3-[(1S,2R)-6,7-dimethoxy-2-methyl-1-(3,4,5-trimethoxyphenyl)-1,2,3,4-tetrahydro-2-isoquinolinio]propyl}-1-{3-{(1R,2S)-6,7-dimethoxy-2-methyl-1-[(3,4,5-trimethoxyphenyl)methyl]-1,2,3,4-tetrahydro-2-isoquinolinio}propyl}butanedioate dichloride The product from step a (3.0 g, 4.85 mmol) was treated with oxalyl chloride and then reacted with the product mixture from Synthetic Example 1, step a (2.44 g, 4.37 mmol) as described in Synthetic Example 2, step c. The reaction mixture was concentrated and the resulting material was purified by MPLC as described in Synthetic Example 1, step C. Lyophilization provided the title product as a white solid (1.3 g, 37% yield): the spectral data were identical to that of the title product from Synthetic Example 5, step c.

The following compounds were prepared by procedures similar to Synthetic Example 6:

Example 6.02

2,2-Difluoro-4-{3-[(1S,2S)-6,7-dimethoxy-2-methyl-1-(3,4,5-trimethoxyphenyl)-1,2,3,4-tetrahydro-2-isoquinolinio]propyl}-1-{3-{(1R,2S)-6,7-dimethoxy-2-methyl-1-[(3,4,5-trimethoxyphenyl)methyl]-1,2,3,4-tetrahydro-2-isoquinolinio}propyl}butanedioate dichloride MS m/z 498 ($M^{2+}$, 100).

Example 6.03

(2RS)-4-{3-[(1S,2R)-6,7-Dimethoxy-2-methyl-1-(3,4,5-trimethoxyphenyl)-1,2,3,4-tetrahydro-2-isoquinolinio]

propyl}-1-{3-{(1R,2S)-6,7 -dimethoxy-2-methyl-1-[(3,4,5-trimethoxyphenyl)methyl]-1,2,3,4-tetrahydro-2-isoquinolinio}propyl}-2-fluorobutanedioate dichloride
MS m/z 489 ($M^{2+}$, 55).

Example 6.04

(2RS)-4-{3-[(1S,2S)-6,7-Dimethoxy-2-methyl-1-(3,4,5 trimethoxyphenyl)-1,2,3,4-tetrahydro-2-isoquinolinio]propyl}-1-{3-{(1R,2S)-6,7-dimethoxy-2-methyl-1-[(3,4,5-trimethoxyphenyl)methyl]-1,2,3,4-tetrahydro-2-isoquinolinio}propyl}-2-fluorobutanedioate dichloride
MS m/z 489 ($M^{2+}$, 30).

SYNTHETIC EXAMPLE 7

Alternative method for the preparation of the compounds of Examples 5.01 and 6.01

Example 7.01

(a) 2,2-Difluoro-4-{3-[(1S,2R)-6,7-dimethoxy-2-methyl-1-(3,4,5-trimethoxyphenyl)-1,2,3,4-tetrahydro-2-isoquinolinio]propyl}-1-{3-{(1R,2S)-6,7dimethoxy-2-methyl-1-[(3,4,5-trimethoxyphenyl)methyl]-1,2,3,4-tetrahydro-2-isoquinolinio} propyl}butanedioate dichloride
Neat oxalyl chloride (25 mL, 0.28 mol) was added dropwise to a solution of the product from Synthetic Example 6, step a (7.0 g. I 1.0 mmol) in DCE (150 mL). The solution was stirred at rt for 3.5 h. The solvent and excess oxalyl chloride were removed at reduced pressure and the remaining foam was reconstituted in DCE (35 mL). A solution of the product from Synthetic Example 3, step c (4.7 g, 10.0 mmol) in DCE (35 mL) was added and the reaction mixture was stirred overnight at rt. The solvent was evaporated and the product was purified by MPLC as described in Synthetic Example 1, step c. Lyophilization provided the title product as a white solid (5.63 g, 53% yield) with spectral data identical to that of the title product from Synthetic Example 5, step c.

The following compound was prepared by procedures similar to Synthetic Example 7:

Example 7.02

2,2-Difluoro-4-{3-[(1S,2R)-6,7-dimethoxy-2-methyl-1-(3,4,5-trimethoxyphenyl)-1,2,3,4-tetrahydro-2-isoquinolinio]propyl}-1-{3-{(1R,2S)-2-methyl-6,7,8-trimethoxy-1-[(3,4,5-trimethoxyphenyl)methyl]-1,2,3,4-tetrahydro-2-isoquinolinio}propyl}butanedioate dichloride
MS m/z 513 ($M^{2+}$, 100).

SYNTHETIC EXAMPLE 8

Example 8.01

(Z)4-{3-[(1S,2R)-6,7-Dimethoxy-2-methyl-1-(3,4,5-trimethoxyphenyl)-1,2,3,4-tetrahydro-2-isoquinolinio]propyl}-1-{3-{(1R,2S)-6,7-dimethoxy-2-methyl-1-[(3,4,5-trimethoxyphenyl)methyl]-1,2,3,4-tetrahydro-2-isoquinolinio}propyl}-2-fluoro-2-butenedioate dichloride
Solid $K_2CO_3$ (97 mg, 0.702 mmol) was added to a solution of the title product from Synthetic Example 7 (750 mg, 0.702 mmol) in DMF (5 mL) and the mixture was stirred at rt for 1 h and then filtered. The filtrate was diluted with $CHCl_3$ (50 mL) and washed with 1:1 brine/$H_2O$ (pH~1). The organic layer was dried and concentrated and the residue was triturated with $Et_2O$ and purified as described in Synthetic Example 1, step c. The title product was obtained as a white powder (404 mg, 0.385 mmol, 52% yield): MS m/z 488 ($M^{2+}$, 80).

The following compound was prepared by a procedure similar to Synthetic Example 8:

Example 8.02

(Z)4-{3-[(1S,2R)-6,7-Dimethoxy-2-methyl-1-(3,4,5-trimethoxyphenyl)-1,2,3,4-tetrahydro-2-isoquinoiinio]propyl}-1-{3-{(1R,2S)-2-methyl-6,7,8-trimethoxy-1-[(3,4,5-trimethoxyphenyl)methyl]-1,2,3,4-tetrahydro-2-isoquinolinio}propyl}-2-fluoro-2-butenedioate dichloride Anal. Calcd for $C_{54}H_{71}N_2O_{15}Cl_2Fo5H_2O$: C, 55.52; H, 6.99; N, 2.40; Cl, 6.07. Found: C, 55.52; H, 6.96; N, 2.40; Cl, 6.15.

Biological Activity

Cats were anesthetized with alpha-chloralose (80 mg/kg) and pentobarbital (10 mg/kg) i.p. See J. J. Savarese *Anesthesia and Analgesia,* Vol. 52, No. 6, November–December, (1973). Square-wave stimuli were applied at supramaximal voltage to the peroneal nerve at 0.15 Hz and the evoked twitches of the tibialis anterior muscle were recorded.

Rhesus monkeys were anesthetized with ketamine (5 mg/Kg) and pentobarbitol (5 mg/Kg) given intramuscularly or intravenously. Anesthesia was maintained with a mixture of halothane (0.25–0.75%), nitrous oxide (60%) and oxygen (40%). The common peroneal nerve was stimulated supramaximally with square wave pulses of 0.2 m sec duration at a rate of 0.15 Hz. Twitch contractions were recorded via the tendon of the extensor digitorum muscle.

In all animals, the trachea was intubated and ventilation was controlled at 12–15 ml/kg, 18–24 breaths per minute. Animals not receiving inhalation anesthetics were ventilated with room air. The left femoral vein and artery were cannulated for drug administration and for recording or arterial pressure, respectively. Compounds of Formula I listed in Table 1 were administered intravenously. The $ED_{95}$, i.e., the dose required to produce 95% block of the twitch response of compounds of Formula (I) is provided in Table 1. Absence of data for particular parameters of particular example numbers indicates that data were not available.

TABLE 1

Neuromuscular Blocking Activity in Rhesus Monkey

| Example No. | ED95 (mg/kg) | Onset (min) | Duration (min) | Hist Rel (mg/kg) | Comment |
|---|---|---|---|---|---|
| Example 1.01 | 0.1–0.15 | 1.2–1.5 | 3.5–7.0 | 3.2–6.4 | |
| Example 1.02 | 0.3 | 0.8 | 3.1 | | |
| Example 1.03 | 0.07 | | 10.5 | 1.2 | |
| Example 1.04 | 0.06 | | 9.5 | 1.2–1.6 | |
| Example 2.01 | 0.05-0.08 | 1 | 5.5 | 3.2–6.4 | Same as 3.01, 4.01 |
| Example 2.02 | 0.3 | | 3.5 | | |
| Example 4.02 | 0.3 | | 3.5 | | |
| Example 5.01 | 0.05–0.07 | 1 | 6.0 | 3.2–6.4 | Same as 6.01, 7.01 |
| Example 6.02 | 0.25 | | 7.0 | | |
| Example 6.03 | 0.04 | | 32.0 | | |
| Example 6.04 | 0.3 | | 27.0 | | |
| Example 7.02 | 0.035 | | 9.5 | 3.2 | |
| Example 8.01 | 0.12 | 1 | 4.0 | 6.4 | |
| Example 8.02 | 0.06 | | 8.0–9.0 | 3.2 | |

What is claimed is:
1. A compound of Formula (I)

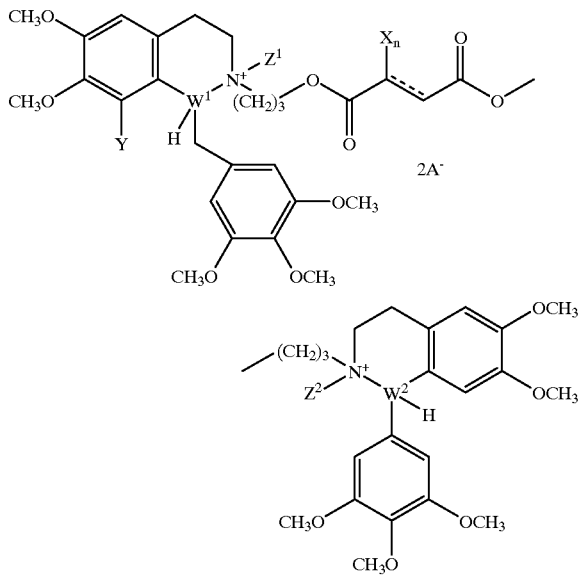

wherein:
X is halogen;
h is from 1 to 2;
Y is hydrogen or methoxy;
$Z^1$ and $Z^2$ are methyl;
$W^1$ and $W^2$ are carbon; and
A is a pharmaceutically acceptable anion.

2. A compound of Formula (I) according to claim 1 which includes:
(Z)-2-Chloro-4-{3-[(1S,2R)-6,7-dimethoxy-2-methyl-1-(3,4,5-trimethoxyphenyl)-1,2,3,4-tetrahydro-2-isoquinolinio]propyl}-1-{3-{(1R,2S)-6,7-dimethoxy-2-methyl-1 -[(3,4,5-trimethoxyphenyl)methyl]-1,2,3,4-tetrahydro-2-isoquinolinio}propyl}-2-butenedioate dichloride,
2,2-Difluoro-4-{3-[(1S,2R)-6,7-dimethoxy-2-methyl-1-(3,4,5-trimethoxyphenyl)-1,2,3,4-tetrahydro-2-isoquinolinio]propyl}1-{3-{(1R, 2S)-6,7-dimethoxy-2-methyl-1-[(3,4,5-trimethoxyphenyl)methyl]-1,2,3,4-tetrahydro-2-isoquinolinio}propyl}-butanedioate dichloride;,
(Z)-4-{3-[(1S,2R)-6,7-Dimethoxy-2-methyl-1-(3,4,5-trimethoxyphenyl)-1,2,3,4-tetrahydro-2-isoquinolinio]propyl}-1-{3-{(1R,2S)-6,7-dimethoxy-2-methyl-1-[(3,4,5-trimethoxyphenyl)methyl]-1,2,3,4-tetrahydro-2-isoquinolinio}propyl}-2-fluoro-2-butenedioate dichloride and
2,2-Difluoro-4-{3-[(1S,2R)-6,7-dimethoxy-2-methyl-1-(3,4,5-trimethoxyphenyl)-1,2,3,4-tetrahydro-2-isoquinolinio]propyl}-1-{3-{(1R,2S)-2-methyl-6,7,8-trimethoxy-1-[(3,4,5-trimethoxyphenyl)methyl]-1,2,3,4-tetrahydro-2- isoquinolinio}propyl}butanedioate dichloride.

3. A pharmaceutical composition comprising a compound acccording to claim 1 in association with one or more pharmaceutically acceptable carriers.

4. A method of inducing neuromuscular paralysis in a mammal comprising administering to said mammal an effective neuromuscular paralyzing amount of a compound according to claim 1.

5. A compound of Formula (II)

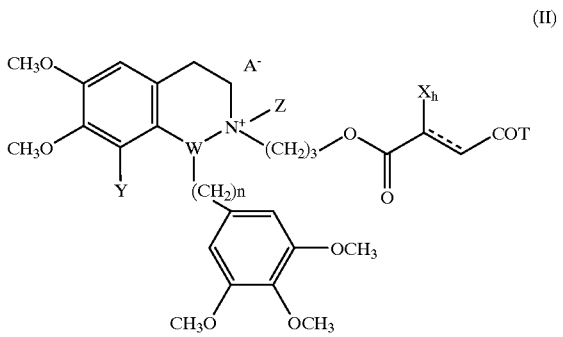

wherein:
T is hydroxyl or halide;
Y is hydrogen or methoxy;
Z is methyl;
W is carbon;
X is halogen;
n is 0 or 1;
h is 1 or 2; and
A is a pharmaceutically acceptable anion.

6. A process for the preparation of a compound of Formula (Ib)

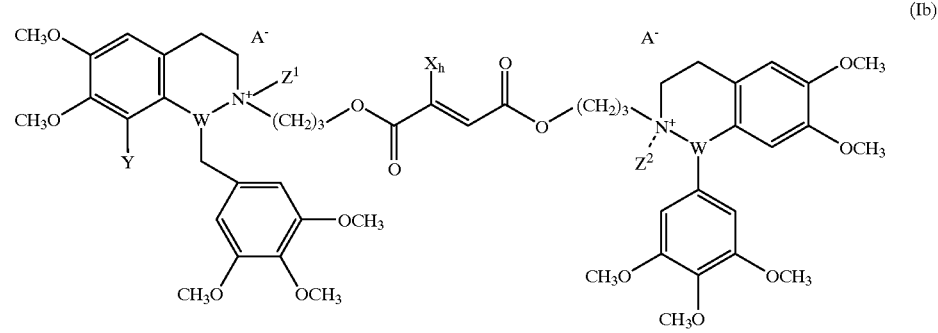

wherein
 h is 1; and
 X is halogen;
 Y is hydrogen or methoxy;
 $Z^1$ and $Z^2$ are methyl;
 $W^1$ and $W^2$ are carbon;
 and A is a pharmaceutically acceptable anion
which comprises reacting a compound of Formula (Ia)

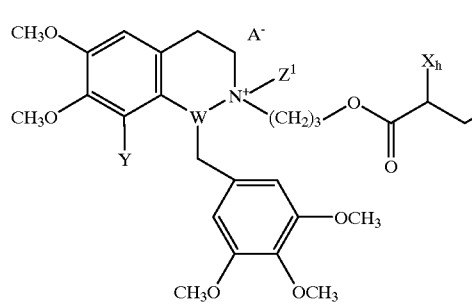

(Ia)

wherein:

h is 2; and
 X, Y, $Z^1$, $Z^2$, $W^1$, $W^2$, and A are as defined herein with a base in a polar aprotic solvent.

7. A process for the preparation of a compound of Formula (I)

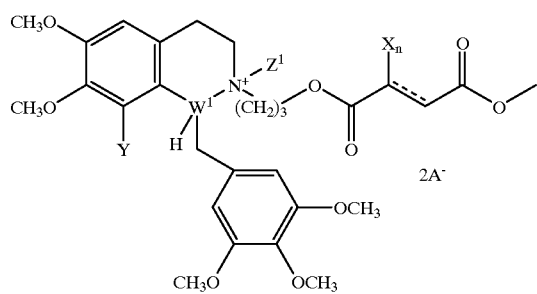

(I)

wherein:
 X is halogen;
 h is from 1 to 2;
 Y is hydrogen or methoxy;
 $Z^1$ and $Z^2$ are methyl;
 $W^1$ and $W^2$ are carbon; and
 A is a pharmaceutically acceptable anion comprising reacting a compound of Formula (II)

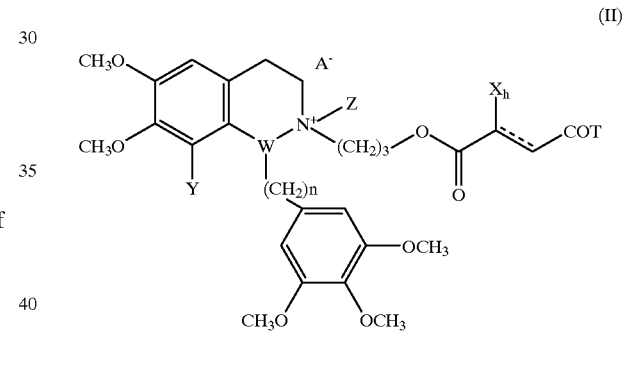

(II)

wherein:
 T is hydrogen hydroxyl or halide;
 X is halogen;
 Y is hydrogen or methoxy;
 Z is methyl;
 W is carbon;
 n is 0 or 1;
 h is 1 or 2; and
 A is a pharmaceutically acceptable anion
with a compound of Formula (III)

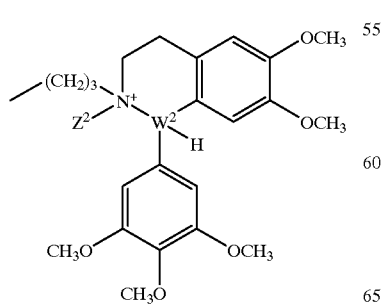

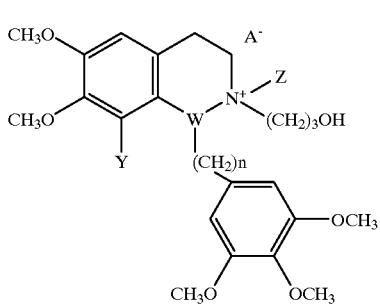

(III)

wherein:
  Y is hydrogen or methoxy;
  Z is methyl;
  W is carbon;
  n is 0 or 1; and
  A is a pharmaceutically acceptable anion in an organic solvent.

* * * * *